(12) United States Patent
Schmidt et al.

(10) Patent No.: US 10,844,006 B2
(45) Date of Patent: Nov. 24, 2020

(54) TRISAMIDE COMPOUNDS AND COMPOSITIONS COMPRISING THE SAME

(71) Applicant: Milliken & Company, Spartanburg, SC (US)

(72) Inventors: Hans-Werner Schmidt, Bayreuth (DE); Daniel Kremer, Bayreuth (DE)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 15/453,255

(22) Filed: Mar. 8, 2017

(65) Prior Publication Data

US 2017/0260129 A1   Sep. 14, 2017

Related U.S. Application Data

(60) Provisional application No. 62/308,892, filed on Mar. 16, 2016, provisional application No. 62/305,547, filed on Mar. 9, 2016.

(51) Int. Cl.
| | |
|---|---|
| *C07C 233/62* | (2006.01) |
| *C07D 233/62* | (2006.01) |
| *C08K 5/20* | (2006.01) |
| *C08L 23/10* | (2006.01) |

(52) U.S. Cl.
CPC .......... *C07C 233/62* (2013.01); *C07D 233/62* (2013.01); *C08K 5/20* (2013.01); *C07C 2601/14* (2017.05); *C08L 23/10* (2013.01)

(58) Field of Classification Search
CPC ..... C07C 233/57; C07C 233/62; C08L 23/10; C08K 5/20
See application file for complete search history.

(56) References Cited

U.S. PATENT DOCUMENTS

| 2,771,487 | A | * | 11/1956 | Morris | .................... | C07C 51/36 |
| | | | | | | 106/310 |
| 2004/0063830 | A1 | | 4/2004 | Schmidt et al. | | |
| 2005/0143510 | A1 | * | 6/2005 | Nakayama | ............ | C08F 297/08 |
| | | | | | | 524/425 |
| 2007/0149663 | A1 | * | 6/2007 | Schmidt | ............... | C08K 5/0083 |
| | | | | | | 524/227 |

FOREIGN PATENT DOCUMENTS

| EP | 1 507 825 | 11/2006 |
| WO | WO 03/102069 A1 | 12/2003 |
| WO | WO 2004/072168 A2 | 8/2004 |
| WO | WO 2008/122525 A1 | 10/2008 |

OTHER PUBLICATIONS

PCT/US2017/021321 International Search Report, filed Mar. 8, 2017, 5 pages.
PCT/US2017/021321 Written Opinion of the International Searching Authority, 7 pages.
Abraham, F. et al., *Macromol. Chem. Phys.* 2010, 211, 171-181.
Blumenhofer, M. et al., *Macromolecules* 2005, 38, 3688-3695.

* cited by examiner

*Primary Examiner* — Kregg T Brooks
(74) *Attorney, Agent, or Firm* — Robert M. Lanning

(57) ABSTRACT

Provided are trisamide compounds and compositions containing the same. In an embodiment, the trisamides are represented by the following formula:

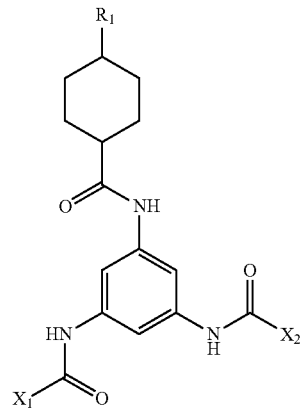

wherein $R_1$ represents a univalent group other than hydrogen, and $X_1$ and $X_2$ represent independently selected univalent groups.

11 Claims, No Drawings

TRISAMIDE COMPOUNDS AND COMPOSITIONS COMPRISING THE SAME

CROSS-REFERENCE TO RELATED PATENT APPLICATIONS

This applications claims, pursuant to 35 U.S.C. § 119(e), priority to and the benefit of the filing date of U.S. Patent Application No. 62/305,547 filed on Mar. 9, 2016 and U.S. Patent Application No. 62/308,892 filed on Mar. 16, 2016, both of which applications are herein incorporated by reference.

TECHNICAL FIELD OF THE INVENTION

This application relates to trisamide compounds and compositions comprising the same.

BACKGROUND

Polymer resins are widely applied in a variety of areas, e.g. because of excellent processability, mechanical properties, especially on a relative weight basis, or electrical properties, etc. Although the polymers themselves may have beneficial properties, additives may be used to further enhance those properties and/or mitigate shortcomings.

BRIEF SUMMARY OF THE INVENTION

In a first embodiment, the present invention provides a trisamide compound according to the following general formula (I):

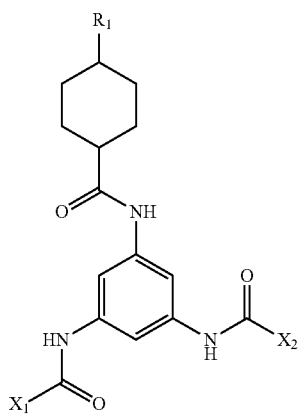

wherein $R_1$ represents a univalent group other than hydrogen; $X_1$ represents a univalent group; and $X_2$ represents a univalent group.

In a second embodiment, the invention provides a composition comprising one or more compounds according to formula (I). In a more particular embodiment, the composition further comprises a polymer.

DETAILED DESCRIPTION OF THE INVENTION

In a first embodiment, the present invention provides a trisamide compound according to the following general formula (I):

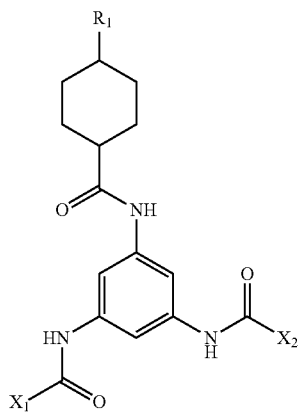

wherein $R_1$, $X_1$, and $X_2$ each represent univalent groups.

In a preferred embodiment, $R_1$ represents a univalent group other than hydrogen. In a more specific preferred embodiment, $R_1$ is a univalent group selected from the group consisting of: $C_1$-$C_{20}$ alkyl groups or $C_1$-$C_{20}$ alkyl groups substituted by one or more hydroxy; $C_2$-$C_{20}$ alkenyl groups unsubstituted or substituted by one or more hydroxy; $C_2$-$C_{20}$ alkyl groups interrupted by oxygen or sulfur; $C_1$-$C_{20}$ alkyl groups substituted by one or more halogens; halogens; trimethylsilyl; and cyano.

In another preferred embodiment, $R_1$ is a univalent group selected from the group consisting of: $C_1$-$C_6$ alkyl groups; branched $C_3$-$C_{20}$ alkyl groups unsubstituted or substituted by one or more hydroxy; $C_1$-$C_{12}$ alkyl groups substituted by one or more halogens; halogens; trimethylsilyl; and cyano.

In another preferred embodiment, $R_1$ is a univalent group selected from the group consisting of: $C_1$-$C_3$ alkyl groups; branched $C_3$-$C_{12}$ alkyl groups; fluorine (F), chlorine (Cl); and trimethylsilyl.

In a particularly preferred embodiment, $R_1$ is a univalent group selected from the group consisting of branched $C_3$-$C_5$ alkyl groups.

In the compounds of formula (I), the substituents attached to the cyclohexanediyl ring can be arranged in any suitable position relative to each other. In one embodiment, $R_1$ is in the cis position relative to the bond with the carbonyl carbon. Or, to put it another way, the hydrogen atoms at the 1- and 4-positions on the cyclohexanediyl ring are in the cis position relative to each other. In another embodiment, $R_1$ is in the trans position relative to the bond with the carbonyl carbon. Or, to put it another way, the hydrogen atoms at the 1- and 4-positions on the cyclohexanediyl ring are in the trans position relative to each other.

As noted above, $X_1$ and $X_2$ represent univalent groups. $X_1$ and $X_2$ can be the same or different and can be any suitable univalent groups. In a preferred embodiment, $X_1$ and $X_2$ are univalent groups independently selected from the group consisting of:
$C_1$-$C_{20}$ alkyl groups unsubstituted or substituted by one or more hydroxy;

$C_2$-$C_{20}$ alkenyl groups unsubstituted or substituted by one or more hydroxy;
$C_2$-$C_{20}$ alkyl groups interrupted by oxygen or sulfur;
$C_3$-$C_5$ cycloalkyl groups unsubstituted or substituted by one or more $C_1$-$C_{20}$ alkyl groups;
$C_6$ cycloalkyl groups unsubstituted or substituted by one or more $C_1$-$C_{20}$ alkyl groups in the 1, 2, 3, 5 or 6 position;
$C_7$-$C_{12}$ cycloalkyl groups unsubstituted or substituted by one or more $C_1$-$C_{20}$ alkyl groups;
($C_3$-$C_{12}$ cycloalkyl)-$C_1$-$C_{10}$ alkyl groups unsubstituted or substituted by one or more $C_1$-$C_{20}$ alkyl groups;
bis[$C_3$-$C_{12}$ cycloalkyl]-$C_1$-$C_{10}$ alkyl groups unsubstituted or substituted by one or more $C_1$-$C_{20}$ alkyl groups;
bicyclic or tricyclic hydrocarbon groups with 5 to 20 carbon atoms unsubstituted or substituted by one or more $C_1$-$C_{20}$ alkyl groups;
phenyl unsubstituted or substituted by one or more groups selected from $C_1$-$C_{20}$ alkyl groups, $C_1$-$C_{20}$ alkoxy groups, $C_1$-$C_{20}$ alkylamino groups, di($C_1$-$C_{20}$ alkyl)amino groups, hydroxy and nitro;
phenyl-$C_1$-$C_{20}$ alkyl groups unsubstituted or substituted by one or more groups selected from $C_1$-$C_{20}$ alkyl groups, $C_3$-$C_{12}$ cycloalkyl groups, phenyl, $C_1$-$C_{20}$ alkoxy groups and hydroxy;
phenylethenyl unsubstituted or substituted by one or more $C_1$-$C_{20}$ alkyl groups; biphenyl-($C_1$-$C_{10}$ alkyl) groups unsubstituted or substituted by one or more $C_1$-$C_{20}$ alkyl groups;
naphthyl unsubstituted or substituted by one or more $C_1$-$C_{20}$ alkyl groups;
naphthyl-$C_1$-$C_{20}$ alkyl groups unsubstituted or substituted by one or more $C_1$-$C_{20}$ alkyl groups;
naphthoxymethyl unsubstituted or substituted by one or more $C_1$-$C_2$ alkyl groups; biphenylenyl, flourenyl, anthryl;
5- to 6-membered heterocylic groups unsubstituted or substituted by one or more $C_1$-$C_{20}$ alkyl groups;
$C_1$-$C_{20}$ hydrocarbon groups containing one or more halogens; and
tri($C_1$-$C_{10}$ alkyl)silyl($C_1$-$C_{10}$ alkyl) groups.

In a more preferred embodiment, at least one of $X_1$ and $X_2$ is a univalent group selected from the group consisting of: $C_1$-$C_{20}$ alkyl groups; $C_2$-$C_{20}$ alkenyl groups; $C_3$-$C_5$ cycloalkyl groups unsubstituted or substituted by one $C_1$-$C_{10}$ alkyl groups; $C_6$ cycloalkyl groups unsubstituted or substituted by one $C_1$-$C_{10}$ alkyl group in the 1, 2 or 3 position; $C_7$-$C_{12}$ cycloalkyl groups unsubstituted or substituted by one $C_1$-$C_{10}$ alkyl group; ($C_3$-$C_{12}$ cycloalkyl)-$C_1$-$C_{10}$ alkyl groups unsubstituted or substituted by one or more $C_1$-$C_{20}$ alkyl groups; phenyl unsubstituted or substituted by one group selected from $C_1$-$C_{10}$ alkyl groups, $C_1$-$C_{10}$ alkoxy groups, $C_1$-$C_{10}$ alkylamino groups, di($C_1$-$C_{10}$ alkyl)amino groups; and biphenyl-($C_1$-$C_{10}$ alkyl) groups unsubstituted or substituted by one or more $C_1$-$C_{20}$ alkyl groups;

In another preferred embodiment at least one of $X_1$ and $X_2$ is a univalent group selected from the group consisting of $C_1$-$C_{10}$ alkyl groups, $C_3$-$C_5$ cycloalkyl groups unsubstituted or substituted by one $C_1$-$C_4$ alkyl group, and $C_7$-$C_{10}$ cycloalkyl groups unsubstituted or substituted by one $C_1$-$C_4$ alkyl group.

In a more preferred embodiment, at least one of $X_1$ and $X_2$ is a univalent group selected from the group consisting of $C_1$-$C_{10}$ alkyl groups. In another preferred embodiment, at least one of $X_1$ and $X_2$ is a univalent group selected from the group consisting of branched $C_3$-$C_{10}$ alkyl groups having a tertiary or quaternary C atom in position 1, such as —C(CH$_3$)$_2$—H and —C(CH$_3$)$_2$—($C_1$-$C_7$ alkyl).

Examples of $C_1$-$C_{20}$ alkyl groups (e.g., branched $C_3$-$C_{20}$ alkyl groups) unsubstituted or substituted by one or more hydroxy (e.g., 1, 2 or 3 hydroxy) suitable for the compounds of the invention include, but are not limited to, ethyl, n-propyl, 1-methylethyl, n-butyl, 2-methylpropyl, 1-methylpropyl, tert-butyl, pentyl, 1-methylbutyl, 2-methylbutyl, 3-methylbutyl, 1,1-dimethylpropyl, 1-ethylpropyl, tert-butylmethyl, hexyl, 1-methylpentyl, heptyl, isoheptyl, 1-ethylhexyl, 2-ethylpentyl, 1-propylbutyl, octyl, nonyl, isononyl, neononyl, 2,4,4-trimethylpentyl, undecyl, tridecyl, pentadecyl, heptadecyl, hydroxymethyl and 1-hydroxyethyl.

Examples of $C_2$-$C_{20}$ alkenyl groups unsubstituted or substituted by one or more hydroxy (e.g., 1, 2 or 3 hydroxy) suitable for the compounds of the invention include, but are not limited to, 9-decenyl, 8-heptadecenyl and 11-hydroxy-8-heptadecenyl.

Examples of $C_2$-$C_{20}$ alkyl groups interrupted by oxygen suitable for the compounds of the invention include, but are not limited to, t-butoxymethyl, t-butoxyethyl, t-butoxypropyl and t-butoxybutyl.

Examples of $C_2$-$C_{20}$ alkyl groups interrupted by sulfur suitable for the compounds of the invention include, but are not limited to, (H$_3$C)$_3$C—S—CH$_2$—, (H$_3$C)$_3$C—S—C$_2$H$_4$—, (H$_3$C)$_3$C—S—C$_3$H$_6$— and (H$_3$C)$_3$C—S—C$_4$H$_8$—.

Examples of $C_3$-$C_5$ cycloalkyl groups unsubstituted or substituted by one or more $C_1$-$C_{20}$ alkyl groups (e.g., 1, 2, 3 or 4 $C_1$-$C_4$ alkyl groups) suitable for the compounds of the invention include, but are not limited to, cyclopropyl, 3-methylcyclopropyl, 2,2,3,3-tetramethylcyclopropyl, cyclobutyl, and cyclopentyl.

Examples of cyclohexyl groups unsubstituted or substituted by one or more $C_1$-$C_{20}$ alkyl groups in the 1, 2 or 3 positions (e.g., 1, 2 or 3 $C_1$-$C_4$ alkyl groups) suitable for the compounds of the invention include, but are not limited to, cyclohexyl, 1,2,3-trimethylcyclohexyl and 2,3-dimethylcyclohexyl.

Examples of $C_7$-$C_{12}$ cycloalkyl groups unsubstituted or substituted by one or more $C_1$-$C_{20}$ alkyl groups (e.g., 1, 2, 3 or 4 $C_1$-$C_4$ alkyl groups) suitable for the compounds of the invention include, but are not limited to, cycloheptyl, 1,2,3-trimethylcycloheptyl and 2,3-dimethylcycloheptyl.

Examples of ($C_3$-$C_{12}$ cycloalkyl)-$C_1$-$C_{10}$ alkyl groups unsubstituted or substituted by one or more $C_1$-$C_{20}$ alkyl groups (e.g., 1, 2 or 3 $C_1$-$C_4$ alkyl groups) suitable for the compounds of the invention include, but are not limited to, cyclopentylmethyl, 2-cyclopentylethyl, cyclohexylmethyl, 2-cyclohexylethyl, 3-cyclohexylpropyl, 4-cyclohexylbutyl and (4-methylcyclohexyl)methyl.

Examples of bis[$C_3$-$C_{12}$ cycloalkyl]-$C_1$-$C_{10}$ alkyl groups unsubstituted or substituted by one or more $C_1$-$C_{20}$ alkyl groups (e.g., 1, 2 or 3 $C_1$-$C_4$ alkyl groups) suitable for the compounds of the invention include, but are not limited to, dicyclohexylmethyl.

Examples of bicyclic or tricyclic hydrocarbon groups with 5 to 20 carbon atoms unsubstituted or substituted by one or more $C_1$-$C_{20}$ alkyl groups (e.g., 1, 2 or 3 $C_1$-$C_4$ alkyl groups) suitable for the compounds of the invention include, but are not limited to, the groups having the structures depicted below:

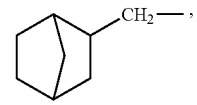

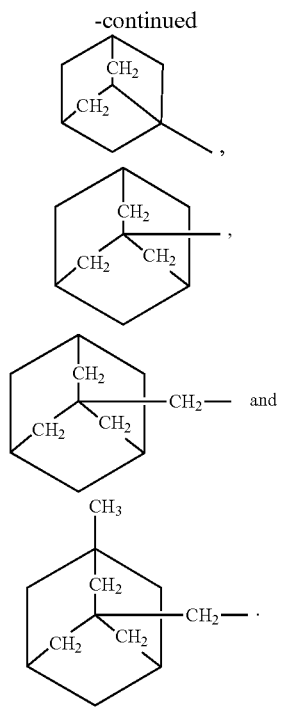

Examples of phenyl unsubstituted or substituted by one or more groups, e.g. 1, 2 or 3 groups, selected from $C_1$-$C_{20}$ alkyl groups, $C_1$-$C_{20}$ alkoxy groups, $C_1$-$C_{20}$ alkylamino groups, di($C_1$-$C_{20}$ alkyl)amino groups, hydroxy and nitro (e.g., $C_1$-$C_4$ alkyl groups, $C_1$-$C_4$ alkoxy groups, $C_1$-$C_4$ alkylamino groups, di($C_1$-$C_4$ alkyl)amino groups, hydroxy and nitro) suitable for the compounds of the invention include, but are not limited to, phenyl, 3-methylphenyl, 3-methoxyphenyl, 4-methylphenyl, 4-ethylphenyl, 4-propylphenyl, 4-isopropylphenyl, 4-tert-butylphenyl, 4-isopropoxyphenyl, 2,3-dimethoxyphenyl, 2-nitrophenyl, 3-methyl-6-nitrophenyl, 4-dimethylaminophenyl, 2,3-dimethylphenyl, 2,6-dimethylphenyl, 2,4-dimethylphenyl, 3,4-dimethylphenyl, 3,5-dimethylphenyl, 3,5-di-tert-butylphenyl, 2,4,6-dimethylphenyl and 3,5-di-tert-butyl-4-hydroxyphenyl.

Examples of phenyl-$C_1$-$C_{20}$ alkyl groups unsubstituted or substituted by one or more groups (e.g., 1, 2 or 3 groups) selected from $C_1$-$C_{20}$ alkyl groups, $C_3$-$C_{12}$ cycloalkyl groups, phenyl, $C_1$-$C_{20}$ alkoxy groups and hydroxy (e.g., $C_1$-$C_4$ alkyl groups, $C_3$-$C_6$ cycloalkyl groups, phenyl, $C_1$-$C_4$ alkoxy groups and hydroxy) suitable for the compounds of the invention include, but are not limited to, benzyl, [alpha]-cyclohexylbenzyl, diphenylmethyl, 1-phenylethyl, [alpha]-hydroxybenzyl, 2-phenylethyl, 2-phenylpropyl, 3-phenylpropyl, 3-methylbenzyl, 3,4-dimethoxybenzyl and 2-(3,4-dimethoxyphenyl)ethyl.

Examples of phenylethenyl unsubstituted or substituted by one or more $C_1$-$C_{20}$ alkyl groups (e.g., 1, 2 or 3 $C_1$-$C_4$ alkyl groups) suitable for the compounds of the invention include, but are not limited to, 2-(4-methylphenyl)ethenyl.

Examples of biphenyl-($C_1$-$C_{10}$ alkyl) groups unsubstituted or substituted by one or more $C_1$-$C_{20}$ alkyl groups (e.g., 1, 2 or 3 $C_1$-$C_4$ alkyl groups) suitable for the compounds of the invention include, but are not limited to, 4-biphenylmethyl.

Examples of naphthyl groups unsubstituted or substituted by one or more $C_1$-$C_{20}$ alkyl groups (e.g., 1, 2 or 3 $C_1$-$C_4$ alkyl groups) suitable for the compounds of the invention include, but are not limited to, 1-naphthyl and 2-naphthyl.

Examples of naphthyl-$C_1$-$C_{20}$ alkyl groups unsubstituted or substituted by one or more $C_1$-$C_{20}$ alkyl groups (e.g., 1, 2 or 3 $C_1$-$C_4$ alkyl groups) suitable for the compounds of the invention include, but are not limited to, 1-naphthylmethyl and 2-naphthylmethyl.

Examples of naphthoxymethyl groups unsubstituted or substituted by one or more $C_1$-$C_{20}$ alkyl groups (e.g., 1, 2 or 3 $C_1$-$C_4$ alkyl groups) suitable for the compounds of the invention include, but are not limited to, 1-naphthoxymethyl.

Examples of biphenylenyl, flourenyl or anthryl groups suitable for the compounds of the invention include, but are not limited to, 2-biphenylenyl, 9-flourenyl, 1-flourenyl and 9-anthryl, respectively.

Examples of 5- to 6-membered heterocyclic groups unsubstituted or substituted by one or more $C_1$-$C_{20}$ alkyl groups (e.g., 1, 2 or 3 $C_1$-$C_4$ alkyl groups) suitable for the compounds of the invention include, but are not limited to, 3-pyridinyl, 4-pyridinyl, 2-hydroxypyridin-3-yl, 3-quinolinyl, 4-quinolinyl, 2-furyl, 3-furyl and 1-methyl-2-pyrroyl.

Examples of $C_1$-$C_{20}$ hydrocarbon groups containing one or more halogens (e.g., 1, 2, 3, 4, 5, or 6 fluorine, chlorine, bromine, or iodine) suitable for the compounds of the invention include, but are not limited to, 1-bromo-2-methylpropyl, dichloromethyl, pentafluoroethyl, 3,5-bis[trifluoromethyl]phenyl, 2,3,5,6-tetrafluoro-p-tolyl, 2,3-dichlorophenyl, 3,4-dichlorophenyl and 2,4-bis[fluoromethyl]phenyl.

In a more specific embodiment of the compounds of formula (I), the invention provides a trisamide compound according to the following general formula (II):

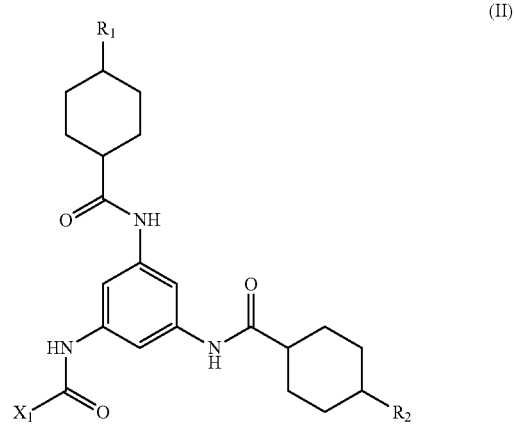

(II)

wherein $R_1$ and $X_1$ are univalent groups independently selected from the groups described above in connection with formula (I), and $R_2$ represents a univalent group independently selected from the groups described above for $R_1$ in connection with formula (I).

In the compounds of formula (II), the substituents attached to each cyclohexanediyl ring can be arranged in any suitable position relative to each other. In one embodiment, $R_1$ and $R_2$ are each in the trans position relative to the bond with the carbonyl carbon attached to the cyclohexanediyl ring. Or, to put it another way, the hydrogen atoms at the 1- and 4-positions of each cyclohexanediyl ring are in the trans position relative to each other. In another embodiment, $R_1$ and $R_2$ are each in the cis position relative to the bond with the carbonyl carbon attached to the cyclohexanediyl ring. Or, to put it another way, the hydrogen atoms at the 1- and 4-positions of each cyclohexanediyl ring are in the cis position relative to each other. In another embodiment, one of $R_1$ and $R_2$ is in the cis position relative to the bond with the carbonyl carbon attached to the cyclohexanediyl ring and the other is in the trans position relative to the bond with the carbonyl carbon attached to the cyclohexanediyl ring. Or, to put it another way, the hydrogen atoms at the 1- and 4-positions of one cyclohexanediyl ring are in the cis position relative to each other, and the hydrogen atoms at the 1- and 4-positions of the other cyclohexanediyl ring are in the trans position relative to each other.

In another more specific embodiment of the compounds of formula (I), the invention provides a trisamide compound according to the following general formula (III):

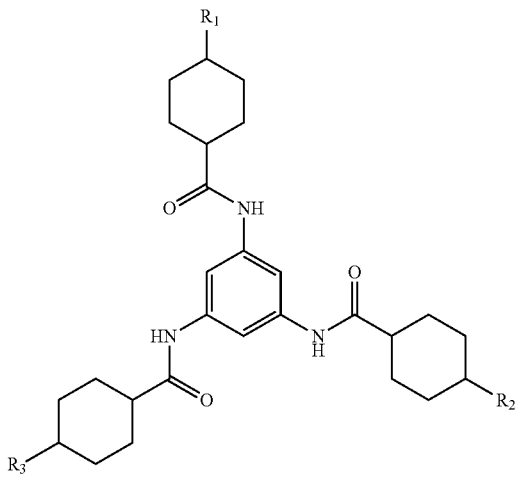

(III)

wherein $R_1$ is a univalent group selected from the groups described above in connection with formula (I), and $R_2$ and $R_3$ are univalent groups independently selected from the groups described above for $R_1$ in connection with formula (I).

In the compounds of formula (III), the substituents attached to each cyclohexanediyl ring can be arranged in any suitable position relative to each other. In one embodiment, each of $R_1$, $R_2$, and $R_3$ is in the trans position relative to the bond with the carbonyl carbon attached to the cyclohexanediyl ring. Or, to put it another way, the hydrogen atoms at the 1- and 4-positions of each cyclohexanediyl ring are in the trans position relative to each other. In another embodiment, each of $R_1$, $R_2$, and $R_3$ is in the cis position relative to the bond with the carbonyl carbon attached to the cyclohexanediyl ring. Or, to put it another way, the hydrogen atoms at the 1- and 4-positions of each cyclohexanediyl ring are in the cis position relative to each other. In yet another embodiment, two of $R_1$, $R_2$, and $R_3$ are in the cis position relative to the bond with the carbonyl carbon attached to the cyclohexanediyl ring and the other is in the trans position relative to the bond with the carbonyl carbon attached to the cyclohexanediyl ring. Or, to put it another way, the hydrogen atoms at the 1- and 4-positions of two cyclohexanediyl rings are in the cis position relative to each other, and the hydrogen atoms at the 1- and 4-positions of the other cyclohexanediyl ring are in the trans position relative to each other. In yet another embodiment, two of $R_1$, $R_2$, and $R_3$ are in the trans position relative to the bond with the carbonyl carbon attached to the cyclohexanediyl ring and the other is in the cis position relative to the bond with the carbonyl carbon attached to the cyclohexanediyl ring. Or, to put it another way, the hydrogen atoms at the 1- and 4-positions of two cyclohexanediyl rings are in the trans position relative to each other, and the hydrogen atoms at the 1- and 4-positions of the other cyclohexanediyl ring are in the cis position relative to each other.

The following are examples of trisamide compounds of formula (I):

cis-4-tert-butylcyclohexylcarbonylamino-3,5-bis[cyclohexylcarbonylamino]benzene;
cis-4-tert-butylcyclohexylcarbonylamino-3,5-bis[cyclopentylcarbonylamino]benzene;
cis-4-tert-butylcyclohexylcarbonylamino-3,5-bis[cycloheptylcarbonylamino]benzene;
cis-4-tert-butylcyclohexylcarbonylamino-3,5-bis[cyclooctylcarbonylamino]benzene;
cis-4-tert-butylcyclohexylcarbonylamino-3,5-bis[methylcarbonylamino]benzene;
cis-4-tert-butylcyclohexylcarbonylamino-3,5-bis[ethylcarbonylamino]benzene;
cis-4-tert-butylcyclohexylcarbonylamino-3,5-bis[n-propylcarbonylamino]benzene;
cis-4-tert-butylcyclohexylcarbonylamino-3,5-bis[iso-propylcarbonylamino]benzene;
cis-4-tert-butylcyclohexylcarbonylamino-3,5-bis[n-butylcarbonylamino]benzene;
cis-4-tert-butylcyclohexylcarbonylamino-3,5-bis[1-methylpropylcarbonylamino]benzene;
cis-4-tert-butylcyclohexylcarbonylamino-3,5-bis[2-methylpropylcarbonylamino]benzene;
cis-4-tert-butylcyclohexylcarbonylamino-3,5-bis[tert-butylpropylcarbonylamino]benzene;
cis-4-tert-butylcyclohexylcarbonylamino-3,5-bis[2,2-dimethylpropyl carbonylamino]benzene;
trans-4-tert-butylcyclohexylcarbonylamino-3,5-bis[cyclohexylcarbonylamino]benzene;
trans-4-tert-butylcyclohexylcarbonylamino-3,5-bis[cyclopentylcarbonylamino]benzene;
trans-4-tert-butylcyclohexylcarbonylamino-3,5-bis[cycloheptylcarbonylamino]benzene;
trans-4-tert-butylcyclohexylcarbonylamino-3,5-bis[cyclooctylcarbonylamino]benzene;
trans-4-tert-butylcyclohexylcarbonylamino-3,5-bis[methylcarbonylamino]benzene;
trans-4-tert-butylcyclohexylcarbonylamino-3,5-bis[ethylcarbonylamino]benzene;
trans-4-tert-butylcyclohexylcarbonylamino-3,5-bis[n-propylcarbonylamino]benzene;
trans-4-tert-butylcyclohexylcarbonylamino-3,5-bis[iso-propylcarbonylamino]benzene;
trans-4-tert-butylcyclohexylcarbonylamino-3,5-bis[n-butylcarbonylamino]benzene;
trans-4-tert-butylcyclohexylcarbonylamino-3,5-bis[1-methylpropylcarbonylamino]benzene;
trans-4-tert-butylcyclohexylcarbonylamino-3,5-bis[2-methylpropylcarbonylamino]benzene;
trans-4-tert-butylcyclohexylcarbonylamino-3,5-bis[tert-butylpropylcarbonylamino]benzene;
trans-4-tert-butylcyclohexylcarbonylamino-3,5-bis[2,2-dimethylpropyl carbonylamino]benzene;
cis-4-iso-propylcyclohexylcarbonylamino-3,5-bis[cyclohexylcarbonylamino]benzene;
cis-4-iso-propylcyclohexylcarbonylamino-3,5-bis[cyclopentylcarbonylamino]benzene;
cis-4-iso-propylcyclohexylcarbonylamino-3,5-bis[cyclooctylcarbonylamino]benzene;

cis-4-iso-propylcyclohexylcarbonylamino-3,5-bis[iso-propylcarbonylamino]benzene;
cis-4-iso-propylcyclohexylcarbonylamino-3,5-bis[1-methylpropylcarbonylamino]benzene;
cis-4-iso-propylcyclohexylcarbonylamino-3,5-bis[2-methylpropylcarbonylamino]benzene;
cis-4-iso-propylcyclohexylcarbonylamino-3,5-bis[tert-butylpropylcarbonylamino]benzene;
cis-4-iso-propylcyclohexylcarbonylamino-3,5-bis[2,2-dimethylpropyl carbonylamino]benzene;
trans-4-iso-propylcyclohexylcarbonylamino-3,5-bis[cyclohexylcarbonylamino]benzene;
trans-4-iso-propylcyclohexylcarbonylamino-3,5-bis[cyclopentylcarbonylamino]benzene;
trans-4-iso-propylcyclohexylcarbonylamino-3,5-bis[cyclooctylcarbonylamino]benzene;
trans-4-iso-propylcyclohexylcarbonylamino-3,5-bis[iso-propylcarbonylamino]benzene;
trans-4-iso-propylcyclohexylcarbonylamino-3,5-bis[1-methylpropylcarbonylamino]benzene;
trans-4-iso-propylcyclohexylcarbonylamino-3,5-bis[2-methylpropylcarbonylamino]benzene;
trans-4-iso-propylcyclohexylcarbonylamino-3,5-bis[tert-butylpropylcarbonylamino]benzene; and
trans-4-iso-propylcyclohexylcarbonylamino-3,5-bis[2,2-dimethylpropyl carbonylamino]benzene.

In a preferred embodiment, the invention provides at least one trisamide compound of formula (I) selected from the group consisting of:
cis-4-tert-butylcyclohexylcarbonylamino-3,5-bis[cyclohexylcarbonylamino]benzene;
cis-4-tert-butylcyclohexylcarbonylamino-3,5-bis[cyclooctylcarbonylamino]benzene;
cis-4-tert-butylcyclohexylcarbonylamino-3,5-bis[iso-propylcarbonylamino]benzene;
cis-4-tert-butylcyclohexylcarbonylamino-3,5-bis[1-methylpropylcarbonylamino]benzene;
cis-4-tert-butylcyclohexylcarbonylamino-3,5-bis[2-methylpropylcarbonylamino]benzene;
cis-4-tert-butylcyclohexylcarbonylamino-3,5-bis[tert-butylcarbonylamino]benzene;
cis-4-tert-butylcyclohexylcarbonylamino-3,5-bis[2,2-dimethylpropyl carbonylamino]benzene;
trans-4-tert-butylcyclohexylcarbonylamino-3,5-bis[cyclohexylcarbonylamino]benzene;
trans-4-tert-butylcyclohexylcarbonylamino-3,5-bis[cyclooctylcarbonylamino]benzene;
trans-4-tert-butylcyclohexylcarbonylamino-3,5-bis[iso-propylcarbonylamino]benzene;
trans-4-tert-butylcyclohexylcarbonylamino-3,5-bis[1-methylpropylcarbonylamino]benzene;
trans-4-tert-butylcyclohexylcarbonylamino-3,5-bis[2-methylpropylcarbonylamino]benzene;
trans-4-tert-butylcyclohexylcarbonylamino-3,5-bis[tert-butylcarbonylamino]benzene;
trans-4-tert-butylcyclohexylcarbonylamino-3,5-bis[2,2-dimethylpropyl carbonylamino]benzene;
cis-4-iso-propylcyclohexylcarbonylamino-3,5-bis[cyclohexylcarbonylamino]benzene;
cis-4-iso-propylcyclohexylcarbonylamino-3,5-bis[iso-propylcarbonylamino]benzene;
cis-4-iso-propylcyclohexylcarbonylamino-3,5-bis[tert-butylcarbonylamino]benzene;
cis-4-iso-propylcyclohexylcarbonylamino-3,5-bis[2,2-dimethylpropyl carbonylamino]benzene;
trans-4-iso-propylcyclohexylcarbonylamino-3,5-bis[cyclohexylcarbonylamino]benzene;
trans-4-iso-propylcyclohexylcarbonylamino-3,5-bis[iso-propylcarbonylamino]benzene;
trans-4-iso-propylcyclohexylcarbonylamino-3,5-bis[tert-butylpropylcarbonylamino]benzene; and
trans-4-iso-propylcyclohexylcarbonylamino-3,5-bis[2,2-dimethylpropyl carbonylamino]benzene.

In another preferred embodiment, the invention provides at least one trisamide compound of formula (I) selected from the group consisting of:
cis-4-tert-butylcyclohexylcarbonylamino-3,5-bis[cyclohexylcarbonylamino]benzene;
cis-4-tert-butylcyclohexylcarbonylamino-3,5-bis[iso-propylcarbonylamino]benzene;
cis-4-tert-butylcyclohexylcarbonylamino-3,5-bis[tert-butylcarbonylamino]benzene;
cis-4-tert-butylcyclohexylcarbonylamino-3,5-bis[2,2-dimethylpropyl carbonylamino]benzene;
trans-4-tert-butylcyclohexylcarbonylamino-3,5-bis[cyclohexylcarbonylamino]benzene;
trans-4-tert-butylcyclohexylcarbonylamino-3,5-bis[iso-propylcarbonylamino]benzene;
trans-4-tert-butylcyclohexylcarbonylamino-3,5-bis[tert-butylcarbonylamino]benzene; and
trans-4-tert-butylcyclohexylcarbonylamino-3,5-bis[2,2-dimethylpropyl carbonylamino]benzene.

The following are examples of trisamide compounds of formula (II):
cyclohexylcarbonylamino-3,5-bis[cis-4-tert-butylcyclohexylcarbonylamino]benzene;
cyclopentylcarbonylamino-3,5-bis[cis-4-tert-butylcyclohexylcarbonylamino]benzene;
cycloheptylcarbonylamino-3,5-bis[cis-4-tert-butylcyclohexylcarbonylamino]benzene;
cyclooctylcarbonylamino-3,5-bis[cis-4-tert-butylcyclohexylcarbonylamino]benzene;
methylcarbonylamino-3,5-bis[cis-4-tert-butylcyclohexylcarbonylamino]benzene;
ethylcarbonylamino-3,5-bis[cis-4-tert-butylcyclohexylcarbonylamino]benzene;
n-propylcarbonylamino-3,5-bis[cis-4-tert-butylcyclohexylcarbonylamino]benzene;
iso-propylcarbonylamino-3,5-bis[cis-4-tert-butylcyclohexylcarbonylamino]benzene;
n-butylcarbonylamino-3,5-bis[cis-4-tert-butylcyclohexylcarbonylamino]benzene;
1-methylpropyl carbonylamino-3,5-bis[cis-4-tert-butylcyclohexylcarbonylamino]benzene;
2-methylpropyl carbonylamino-3,5-bis[cis-4-tert-butylcyclohexylcarbonylamino]benzene;
tert-butylcarbonylamino-3,5-bis[cis-4-tert-butylcyclohexylcarbonylamino]benzene;
2,2-dimethylpropylcarbonylamino-3,5-bis[cis-4-tert-butylcyclohexylcarbonylamino]benzene;
cyclohexylcarbonylamino-3,5-bis[trans-4-tert-butylcyclohexylcarbonylamino]benzene;
cyclopentylcarbonylamino-3,5-bis[trans-4-tert-butylcyclohexylcarbonylamino]benzene;
cycloheptylcarbonylamino-3,5-bis[trans-4-tert-butylcyclohexylcarbonylamino]benzene;
cyclooctylcarbonylamino-3,5-bis[trans-4-tert-butylcyclohexylcarbonylamino]benzene;
methylcarbonylamino-3,5-bis[trans-4-tert-butylcyclohexylcarbonylamino]benzene;
ethylcarbonylamino-3,5-bis[trans-4-tert-butylcyclohexylcarbonylamino]benzene;
n-propylcarbonylamino-3,5-bis[trans-4-tert-butylcyclohexylcarbonylamino]benzene;

iso-propylcarbonylamino-3,5-bis[trans-4-tert-butylcyclohexylcarbonylamino]benzene;
n-butylcarbonylamino-3,5-bis[trans-4-tert-butylcyclohexylcarbonylamino]benzene;
1-methylpropyl carbonylamino-3,5-bis[trans-4-tert-butylcyclohexylcarbonylamino]benzene;
2-methylpropyl carbonylamino-3,5-bis[trans-4-tert-butylcyclohexylcarbonylamino]benzene;
tert-butylcarbonylamino-3,5-bis[trans-4-tert-butylcyclohexylcarbonylamino]benzene;
2,2-dimethylpropylcarbonylamino-3,5-bis[trans-4-tert-butylcyclohexylcarbonylamino]benzene;
cyclohexylcarbonylamino-3-[cis-4-tert-butylcyclohexylcarbonylamino]-5-[trans-tert-butylcyclohexylcarbonylamino]benzene;
cyclohexylcarbonylamino-3-[cis-4-iso-propylcyclohexylcarbonylamino]-5-[trans-tert-butylcyclohexylcarbonylamino]benzene;
cyclohexylcarbonylamino-3-[cis-4-tert-butylcyclohexylcarbonylamino]-5-[trans-iso-propylcyclohexylcarbonylamino]benzene;
2,2-dimethylpropylcarbonylamino-3-[cis-4-tert-butylcyclohexylcarbonylamino]-5-[trans-tert-butylcyclohexylcarbonylamino]benzene;
iso-propylcarbonylamino-3-[cis-4-tert-butylcyclohexylcarbonylamino]-5-[trans-tert-butylcyclohexylcarbonylamino]benzene;
iso-propylcarbonylamino-3-[cis-4-iso-propylcyclohexylcarbonylamino]-5-[trans-tert-butylcyclohexylcarbonylamino]benzene;
iso-propylcarbonylamino-3-[cis-4-tert-butylcyclohexylcarbonylamino]-5-[trans-iso-propylcyclohexylcarbonylamino]benzene;
tert-butylcarbonylamino-3-[cis-4-tert-butylcyclohexylcarbonylamino]-5-[trans-tert-butylcyclohexylcarbonylamino]benzene;
tert-butylcarbonylamino-3-[cis-4-iso-propylcyclohexylcarbonylamino]-5-[trans-tert-butylcyclohexylcarbonylamino]benzene;
tert-butylcarbonylamino-3-[cis-4-tert-butylcyclohexylcarbonylamino]-5-[trans-iso-propylcyclohexylcarbonylamino]benzene;
2,2-dimethylpropylcarbonylamino-3-[cis-4-tert-butylcyclohexylcarbonylamino]-5-[trans-tert-butylcyclohexylcarbonylamino]benzene;
2,2-dimethylpropylcarbonylamino-3-[cis-4-iso-propylcyclohexylcarbonylamino]-5-[trans-tert-butylcyclohexylcarbonylamino]benzene; and
2,2-dimethylpropylcarbonylamino-3-[cis-4-tert-butylcyclohexylcarbonylamino]-5-[trans-iso-propylcyclohexylcarbonylamino]benzene.

In a preferred embodiment, the invention provides at least one trisamide compound of formula (II) selected from the group consisting of:
cyclohexylcarbonylamino-3,5-bis[cis-4-tert-butylcyclohexylcarbonylamino]benzene;
cyclooctylcarbonylamino-3,5-bis[cis-4-tert-butylcyclohexylcarbonylamino]benzene;
methylcarbonylamino-3,5-bis[cis-4-tert-butylcyclohexylcarbonylamino]benzene;
ethylcarbonylamino-3,5-bis[cis-4-tert-butylcyclohexylcarbonylamino]benzene;
iso-propylcarbonylamino-3,5-bis[cis-4-tert-butylcyclohexylcarbonylamino]benzene;
1-methylpropyl carbonylamino-3,5-bis[cis-4-tert-butylcyclohexylcarbonylamino]benzene;
2-methylpropyl carbonylamino-3,5-bis[cis-4-tert-butylcyclohexylcarbonylamino]benzene;
tert-butylcarbonylamino-3,5-bis[cis-4-tert-butylcyclohexylcarbonylamino]benzene;
2,2-dimethylpropylcarbonylamino-3,5-bis[cis-4-tert-butylcyclohexylcarbonylamino]benzene;
cyclohexylcarbonylamino-3,5-bis[trans-4-tert-butylcyclohexylcarbonylamino]benzene;
cyclooctylcarbonylamino-3,5-bis[trans-4-tert-butylcyclohexylcarbonylamino]benzene;
methylcarbonylamino-3,5-bis[trans-4-tert-butylcyclohexylcarbonylamino]benzene;
ethylcarbonylamino-3,5-bis[trans-4-tert-butylcyclohexylcarbonylamino]benzene;
iso-propylcarbonylamino-3,5-bis[trans-4-tert-butylcyclohexylcarbonylamino]benzene;
1-methylpropyl carbonylamino-3,5-bis[trans-4-tert-butylcyclohexylcarbonylamino]benzene;
2-methylpropyl carbonylamino-3,5-bis[trans-4-tert-butylcyclohexylcarbonylamino]benzene;
tert-butylcarbonylamino-3,5-bis[trans-4-tert-butylcyclohexylcarbonylamino]benzene; and
2,2-dimethylpropylcarbonylamino-3,5-bis[trans-4-tert-butylcyclohexylcarbonylamino]benzene.

In another preferred embodiment, the invention provides at least one trisamide compound of formula (II) selected from the group consisting of:
cyclohexylcarbonylamino-3,5-bis[cis-4-tert-butylcyclohexylcarbonylamino]benzene;
cyclooctylcarbonylamino-3,5-bis[cis-4-tert-butylcyclohexylcarbonylamino]benzene;
iso-propylcarbonylamino-3,5-bis[cis-4-tert-butylcyclohexylcarbonylamino]benzene;
1-methylpropyl carbonylamino-3,5-bis[cis-4-tert-butylcyclohexylcarbonylamino]benzene;
tert-butylcarbonylamino-3,5-bis[cis-4-tert-butylcyclohexylcarbonylamino]benzene; and
2,2-dimethylpropylcarbonylamino-3,5-bis[cis-4-tert-butylcyclohexylcarbonylamino]benzene.

The following are examples of trisamide compounds of formula (III):
1,3,5-tris[cis-4-tert-butylcyclohexylcarbonylamino]benzene;
trans-4-tert-butylcyclohexylcarbonylamino-3,5-bis[cis-4-tert-butylcyclohexylcarbonylamino]benzene;
cis-4-tert-butylcyclohexylcarbonylamino-3,5-bis[trans-4-tert-butylcyclohexylcarbonylamino]benzene;
1,3,5-tris[trans-4-tert-butylcyclohexylcarbonylamino]benzene;
1,3,5-tris[cis-4-iso-propylcyclohexylcarbonylamino]benzene;
trans-4-iso-propylcyclohexylcarbonylamino-3,5-bis[cis-4-iso-propylcyclohexylcarbonylamino]benzene;
cis-4-iso-propylcyclohexylcarbonylamino-3,5-bis[trans-4-iso-propylcyclohexylcarbonylamino]benzene;
1,3,5-tris[trans-4-iso-propylcyclohexylcarbonylamino]benzene;
1,3,5-tris[cis-4-n-propylcyclohexylcarbonylamino]benzene;
trans-4-n-propylcyclohexylcarbonylamino-3,5-bis[cis-4-n-propylcyclohexylcarbonylamino]benzene;
cis-4-n-propylcyclohexylcarbonylamino-3,5-bis[trans-4-n-propylcyclohexylcarbonylamino]benzene;
1,3,5-tris[trans-4-n-propylcyclohexylcarbonylamino]benzene;
1,3,5-tris[cis-4-ethylcyclohexylcarbonylamino]benzene;
trans-4-ethylcyclohexylcarbonylamino-3,5-bis[cis-4-ethylcyclohexylcarbonylamino]benzene;

cis-4-ethylcyclohexylcarbonylamino-3,5-bis[trans-4-ethyl-cyclohexylcarbonylamino]benzene;
1,3,5-tris[trans-4-ethylcyclohexylcarbonylamino]benzene;
1,3,5-tris[cis-4-methylcyclohexylcarbonylamino]benzene;
trans-4-methylcyclohexylcarbonylamino-3,5-bis[cis-4-methylcyclohexylcarbonylamino]benzene;
cis-4-methylcyclohexylcarbonylamino-3,5-bis[trans-4-methylcyclohexylcarbonylamino]benzene;
1,3,5-tris[trans-4-methylcyclohexylcarbonylamino]benzene;
trans-4-tert-butylcyclohexylcarbonylamino-3,5-bis[cis-4-iso-propylcyclohexylcarbonylamino]benzene;
cis-4-tert-butylcyclohexylcarbonylamino-3,5-bis[trans-4-iso-propylcyclohexylcarbonylamino]benzene;
trans-4-tert-butylcyclohexylcarbonylamino-3,5-bis[cis-4-n-propylcyclohexylcarbonylamino]benzene;
cis-4-tert-butylcyclohexylcarbonylamino-3,5-bis[trans-4-n-propylcyclohexylcarbonylamino]benzene;
trans-4-tert-butylcyclohexylcarbonylamino-3,5-bis[cis-4-ethylcyclohexylcarbonylamino]benzene;
cis-4-tert-butylcyclohexylcarbonylamino-3,5-bis[trans-4-ethylcyclohexylcarbonylamino]benzene;
trans-4-tert-butylcyclohexylcarbonylamino-3,5-bis[cis-4-methylcyclohexylcarbonylamino]benzene;
cis-4-tert-butylcyclohexylcarbonylamino-3,5-bis[trans-4-methylcyclohexylcarbonylamino]benzene;
trans-4-iso-propylcyclohexylcarbonylamino-3,5-bis[cis-4-tert-butylcyclohexylcarbonylamino]benzene;
cis-4-iso-propylcyclohexylcarbonylamino-3,5-bis[trans-4-tert-butylcyclohexylcarbonylamino]benzene;
trans-4-n-propylcyclohexylcarbonylamino-3,5-bis[cis-4-tert-butylcyclohexylcarbonylamino]benzene;
cis-4-n-propylcyclohexylcarbonylamino-3,5-bis[trans-4-tert-butylcyclohexylcarbonylamino]benzene;
trans-4-ethylcyclohexylcarbonylamino-3,5-bis[cis-4-tert-butylcyclohexylcarbonylamino]benzene;
cis-4-ethylcyclohexylcarbonylamino-3,5-bis[trans-4-tert-butylcyclohexylcarbonylamino]benzene;
trans-4-methylcyclohexylcarbonylamino-3,5-bis[cis-4-tert-butylcyclohexylcarbonylamino]benzene; and
cis-4-methylcyclohexylcarbonylamino-3,5-bis[trans-4-tert-butylcyclohexylcarbonylamino]benzene.

In a preferred embodiment, the invention provides at least one trisamide compound of formula (III) selected from the group consisting of:
1,3,5-tris[cis-4-tert-butylcyclohexylcarbonylamino]benzene;
trans-4-tert-butylcyclohexylcarbonylamino-3,5-bis[cis-4-tert-butylcyclohexylcarbonylamino]benzene;
cis-4-tert-butylcyclohexylcarbonylamino-3,5-bis[trans-4-tert-butylcyclohexylcarbonylamino]benzene;
1,3,5-tris[trans-4-tert-butylcyclohexylcarbonylamino]benzene;
trans-4-tert-butylcyclohexylcarbonylamino-3,5-bis[cis-4-iso-propylcyclohexylcarbonylamino]benzene;
cis-4-tert-butylcyclohexylcarbonylamino-3,5-bis[trans-4-iso-propylcyclohexylcarbonylamino]benzene;
trans-4-iso-propylcyclohexylcarbonylamino-3,5-bis[cis-4-tert-butylcyclohexylcarbonylamino]benzene; and
cis-4-iso-propylcyclohexylcarbonylamino-3,5-bis[trans-4-tert-butylcyclohexylcarbonylamino]benzene.

In another preferred embodiment, the invention provides at least one trisamide compound of formula (III) selected from the group consisting of:
1,3,5-tris[cis-4-tert-butylcyclohexylcarbonylamino]benzene;
trans-4-tert-butylcyclohexylcarbonylamino-3,5-bis[cis-4-tert-butylcyclohexylcarbonylamino]benzene;
cis-4-tert-butylcyclohexylcarbonylamino-3,5-bis[trans-4-tert-butylcyclohexylcarbonylamino]benzene; and
1,3,5-tris[trans-4-tert-butylcyclohexylcarbonylamino]benzene.

In a preferred embodiment of the invention, the trisamide compound is selected from the group consisting of 1,3,5-tris[cis-4-tert-butylcyclohexylcarbonylamino]benzene; trans-4-tert-butylcyclohexylcarbonylamino-3,5-bis[cis-4-tert-butylcyclohexylcarbonylamino]benzene, cis-4-tert-butylcyclohexylcarbonylamino-3,5-bis[trans-4-tert-butylcyclohexylcarbonylamino]benzene; 1,3,5-tris[trans-4-tert-butylcyclohexylcarbonylamino]benzene; and mixtures thereof. In another preferred embodiment of the invention, the trisamide compound is 1,3,5-tris[cis-4-tert-butylcyclohexylcarbonylamino]benzene. In yet another preferred embodiment of the invention, the trisamide compound is trans-4-tert-butylcyclohexylcarbonylamino-3,5-bis[cis-4-tert-butylcyclohexylcarbonylamino]benzene. In yet another preferred embodiment of the invention, the trisamide compound is cis-4-tert-butylcyclohexylcarbonylamino-3,5-bis[trans-4-tert-butylcyclohexylcarbonylamino]benzene. In yet another preferred embodiment of the invention, the trisamide compound is 1,3,5-tris[trans-4-tert-butylcyclohexylcarbonylamino]benzene.

As noted above, the invention also provides a composition comprising at least one trisamide compound of formula (I-III), such as a compound of formula (III). The composition of the invention can comprise any suitable material in addition to the trisamide compound(s) described above. In a preferred embodiment, the composition further comprises a polymer. The polymer present in the composition can be any suitable polymer. Preferably, the polymer is a thermoplastic polymer, such as a polyolefin, polyester, polyamide, polylactic acid, polycarbonate, acrylic polymer, or mixture thereof. More preferably, the polymer is a polyolefin polymer, such as a polypropylene polymer, a polyethylene polymer, a polymethylpentene polymer (e.g., poly(4-methyl-1-pentene)), a polybutylene polymer, a poly(vinyl cyclohexane) polymer, and mixtures thereof. In a preferred embodiment, the polymer is a polypropylene polymer. More preferably, the polymer in the composition is selected from the group consisting of polyproplyne homopolymers (e.g., atactic polypropylene homopolymer, isotactic polypropylene hompolymer, and syndiotactic polypropylene homopolymer), polypropylene copolymers (e.g., polypropylene random copolymers), polypropylene impact copolymers, and mixtures thereof. Suitable polypropylene copolymers include, but are not limited to, random copolymers made from the polymerization of propylene in the presence of a comonomer selected from the group consisting of ethylene, but-1-ene (i.e., 1-butene), and hex-1-ene (i.e., 1-hexene). In such polypropylene random copolymers, the comonomer can be present in any suitable amount, but typically is present in an amount of less than about 10 wt. % (e.g., about 1 to about 7 wt. %). Suitable polypropylene impact copolymers include, but are not limited to, those produced by the addition of a copolymer selected from the group consisting of ethylene-propylene rubber (EPR), ethylenepropylene-diene monomer (EPDM), polyethylene, and plastomers to a polypropylene homopolymer or polypropylene random copolymer. In such polypropylene impact copolymers, the copolymer can be present in any suitable amount, but typically is present in an amount of from about 5 to about 25 wt. %.

The composition of the invention can contain any suitable amount of the trisamide compound(s) described above. In a preferred embodiment, the composition comprises, relative to the total weight of the composition, at least 0.001 wt. % of a trisamide compound of formula (I-III). In another preferred embodiment, the composition comprises, relative to the total weight of the composition, at least 0.01 wt. % of a trisamide compound of formula (I-III). In another preferred embodiment, the composition comprises at least 0.05 wt. %, at least 0.1 wt. %, at least 0.3 wt. %, at least 0.5 wt. %, at least 1 wt. %, at least 5 wt. %, or at least 10 wt. % of a trisamide compound of formula (I-III). In another embodiment the composition comprises, relative to the total weight of the composition, less than 99 wt. % of a trisamide compound of formula (I-III). In another preferred embodiment, the composition comprises less than 95 wt. %, less than 80 wt. %, less than 50 wt. %, less than 25 wt. %, less than 10 wt. %, less than 5 wt. %, less than 2 wt. %, less than 1 wt. %, less than 0.5 wt. %, less than 0.2 wt. %, less than 0.1 wt. %, or less than 0.07 wt. % of a trisamide compound of formula (I-III). In a particularly preferred embodiment, the composition comprises, relative to the total weight of the composition, 0.001 wt. % to 0.5 wt. % (e.g., 0.01 wt. % to 0.5 wt. % or 0.05 wt. % to 0.5 wt. %), 0.001 wt. % to about 0.2 wt. % (e.g., 0.01 wt. % to 0.2 wt. % or 0.05 wt. % to 0.2 wt. %), 0.001 wt. % to 0.1 wt. % (e.g., 0.01 wt. % to 0.1 wt. % or 0.05 wt. % to 0.1 wt. %), or 0.001 wt. % to 0.07 wt. % (e.g., 0.01 wt. % to 0.07 wt. %) of at least one trisamide compound of formula (I-III). As noted above, the composition of the invention can comprise more than one trisamide compound of formula (I-III). In those embodiments in which the composition comprises more than one such trisamide compound, each trisamide compound can be present in an amount falling within one of the ranges recited above, or the combined amount of all trisamide compounds can fall within one of the ranges recited above.

The trisamide compounds of the invention can be synthesized using any suitable process or method. For example, the compounds of formulas (I) and (II) can be synthesized according to methods described in U.S. Pat. Publn. No. 2007/0149663, which is hereby incorporated in its entirety by reference. The compounds of formula (III) can be synthesized, for example, by hydrogenation of 1,3,5-trinitrobenzene, 3,5-dinitroaniline or 1,3-diamino-5-nitrobenzene with hydrogen and an appropriate metal catalyst in an appropriate organic solvent. The thus obtained 1,3,5-triaminobenzene can be isolated or optionally transformed into the corresponding hydrochloride and purified in either form by recrystallization from an appropriate solvent. It is also possible to use the solution of the crude trisamine or the isolated crude trisamine (with or without removal of the water formed in the hydrogenation) for the subsequent acylation reaction. Useful catalysts for the hydrogenation include, but are not limited to, Pd, $PtO_2$, Raney-Nickel etc., preferably the commercially available versions on carbon support. The hydrogenation can be carried out under normal pressure or under elevated pressure at temperatures between, for example, 20 and 120° C., although other procedures can also be employed. Appropriate solvents for the hydrogenation include, but are not limited to, tetrahydrofuran (THF), THF/methanol, dimethylformamide (DMF) or N-methylpyrrolidone (NMP). An alternative procedure for hydrogenation of the 1,3,5-trinitrobenzene, 3,5-dinitroaniline or 1,3-diamino-5-nitrobenzene is reduction with Raney-Nickel and hydrazine as hydrogen source (see e.g. Organikum, Chapter 8.1, Reduktion von Nitroverbindungen und Nitrosoverbindung, Berlin, 1970), or other known standard reductions.

Recrystallization of the 1,3,5-triaminobenzene or hydrochloride thereof can be carried out with, for example, methanol, ethanol or other alcohols.

The free amine (or the amine obtained from the hydrochloride and an appropriate base) can be acylated with a stoichiometric amount or an excess of the corresponding acid chloride, preferably in the presence of an organic or inorganic non-interacting base, such as triethylamine, tributylamine, or pyridine. Alternatively, the free amine (or the amine obtained from the hydrochloride and an appropriate base) can be acylated with a stoichiometric amount or an excess of the anhydride of the carboxylic acid as acylating agent; in which case no or little base is required. The reaction is carried out in the absence or preferably in the presence of a solvent. The preferred reaction temperature depends on the nature of the acylating agents (e.g., 0° C.-100° C.). Isolation/purification of the final product can be carried out by precipitation/recrystallization/washing with an appropriate mixture of, for instance, water/organic solvent or organic solvent/organic solvent or with a pure solvent, such as DMF/water, NMP/water, ethanol, methanol, etc.

The cis- or trans 4-substituted-cyclohexanecarboxylic acids used to make the corresponding acid chlorides can be prepared for example as disclosed in US Pat. Publn. No. 2004/0209858 and R. D. Stolow, *J. Am. Chem. Soc.*, 1959, 81 (21), pp 5806-5811 (both references are hereby incorporated in their entirety by reference).

In the case of benzenetrisamides based on 1,3,5-trisaminobenzene, different activated or non-activated carboxylic acids in different ratios can be used in a statistical synthesis yielding mixtures of the present compounds. One or more isomers can be extracted out of an isomeric mixture by dissolving one or more isomers in a suitable solvent or by sublimation, so that at least one isomer remains.

Mixtures of compounds according to the present invention can be prepared, among other protocols, for example, by the following methods:

a) mixing two or more powdered compounds (powder-powder-mixture of compounds);

b) dissolving two or more compounds in a common solvent and subsequent evaporation of the solvent yielding the compound mixture (mixture of compounds via solution);

c) dissolving one or more compounds in a dispersion comprising one or more compounds and subsequent evaporation of the solvent yielding the compound mixture (mixture of compound via dispersion);

d) in the case of benzenetrisamides based on 1,3,5-trisaminobenzene, different activated or non-activated carboxylic acids in different ratios can be used in a statistical synthesis yielding compound mixtures (compound mixtures via synthesis); and e) extraction of one or more compounds from statistical compounds mixtures, for instance as obtained in d), for example by selective dissolution or sublimation.

The trisamide compounds of the invention can be employed as functional substances for use with a broad range of materials, including glassy and semi-crystalline polymers, elastomers, rubbers, thermosets, and the like. The trisamide compounds can be used by themselves or in combination with other functional substances to enhance, for instance, thermal, optical, electrical, cosmetic and, among other characteristics, mechanical properties of materials to which they may be added, or as processing aid in manufacturing useful objects from such materials. Examples include organogelators, nucleating agents, electret additives, foam nucleation additives, melt- or solution viscosity or flow modifiers, anti-blocking additives, supports for catalysts, precursors for molecular sieves, drug delivery support, supramolecular nanofibers for filtration applications and the like.

The following examples further illustrate the subject matter described above but, of course, should not be construed as in any way limiting the scope thereof.

The following general procedures are used in the examples unless otherwise indicated.

Thermo-Gravimetric Analysis (TGA), Differential Thermal Analysis (DTA)

An automated Mettler Toledo® TGA/SDTA 851e operated in a nitrogen atmosphere is used for the analysis of the thermal stability and the melting temperature. About 10 mg of sample is placed into an aluminum oxide crucible and heated from 30° C. to 700° C. at a rate of 10° C./min. The decomposition temperatures listed are the temperatures at which a 5 wt. % weight loss is detected in the TGA analysis.

Melting Temperatures (TM)

An automated Mettler Toledo DSC 2 operated in nitrogen is used to determine the melting temperatures of the compounds. Therefore about 2 to 10 mg of the compound is weighed in a reusable high pressure crucible (steel) with gold-seal and heated from 50° C. to 365° C. at a rate of 10° C./min. The peak maximum of the endothermic transition is recorded as the melting temperature of the compound.

1H-NMR (Determination of the Cis/Trans-Ratio)

A Bruker Avance Ultrashield 300 was used for recording NMR spectra of the compounds to determine the cis/trans-ratio of the compounds.

Mass Spectroscopy

A FINNIGAN MAT8500 Mass instrument with a MASPEC II data system was used to obtain mass spectroscopic (MS-EI) data.

Example A

This example demonstrates the preparation of 1,3,5-tris[cis-4-tert-butylcyclohexylcarbonylamino]benzene.

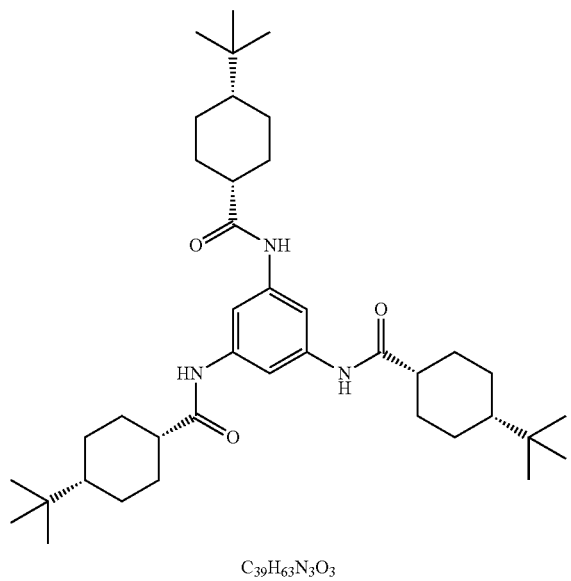 [SMILES: CC(C)(C)[C@H]1CC[C@@H](C(=O)Nc2cc(NC(=O)[C@H]3CC[C@@H](C(C)(C)C)CC3)cc(NC(=O)[C@H]3CC[C@@H](C(C)(C)C)CC3)c2)CC1 ; "C39H63N3O3"]

$C_{39}H_{63}N_3O_3$ a) Preparation of 1,3,5-triaminobenzene:

6 g (33 mmol) of 3,5-dinitroaniline is dissolved in a mixture of 50 ml of methanol and 300 ml of tetrahydrofuran. The mixture is placed in a Buechi glass reactor and 0.6 g of palladium 10 wt % on activated carbon is added. The reactor is closed and under stirring 3 times purged with nitrogen and 3 times with hydrogen. The hydrogenation is carried out at 35° C. and a hydrogen pressure of 3 bar for 12 h. The reaction mixture is transferred under inert atmosphere into a flask and filtered over 40 g of aluminum oxide (Alox N) to remove the activated carbon, the catalyst and water.

b) Preparation of 1,3,5-tris[cis-4-tert-butylcyclohexylcarbonylamino]benzene:

1.76 g (14.3 mmol) of 1,3,5-triaminobenzene and 0.1 g of dry LiCl are added under inert atmosphere to 100 ml of dry N-methylpyrrolidone (NMP) and 30 ml of dry pyridine and cooled to 5° C. 9.55 g (47 mmol) of cis-4-tert-butylcyclohexylcarbonyl chloride is added.

The reaction mixture is heated to 80° C. and stirred overnight. After 12 h the reaction mixture is added to 1500 ml of ice water. The precipitate is filtered off and dried. Customary work-up (recrystallization from N,N-dimethylformamide (DMF)) gives the desired product as a white powder.

Trans-content: 0% (according to $^1$H-NMR).

Melting point: 349° C.

MS(EI): 621 ($M^+$).

Decomposition temperature: 398° C.

Example B

This example demonstrates the preparation of trans-4-tert-butylcyclohexylcarbonylamino-3,5-bis[cis-4-tert-butylcyclohexylcarbonylamino]benzene.

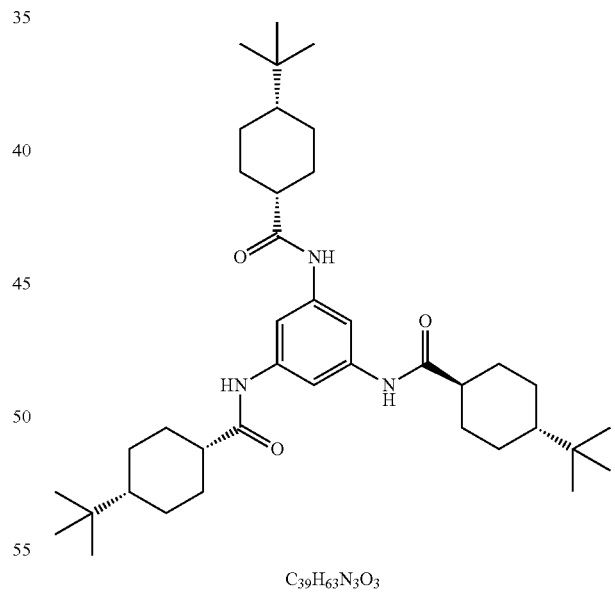

$C_{39}H_{63}N_3O_3$ a) trans-4-tert-butylcyclohexylcarbonylamino-3,5-dinitrobenzene is obtained from 1.11 g (6.1 mmol) of 3,5-dinitroaniline, 1.47 g (7.3 mmol) of trans-4-tert-butylcyclohexylcarbonyl chloride, 5 ml of pyridine, 50 ml of dried THF and 0.1 g of LiCl. The acylation is carried out as described in Example A.

b) 1.70 g (4.8 mmol) of the product obtained under a) is hydrogenated in 200 ml THF p.a. and 50 ml MeOH with 0.1 g Pd/C (10 wt %) at 35° C. in analogy to Example A.

The reaction mixture is transferred under inert atmosphere into a flask and filtered over 40 g of aluminum oxide (Alox N) to remove the activated carbon, the catalyst and water.

c) 1.38 g (13.8 mmol) of trans-4-tert-butylcyclohexylcarbonylamino-3,5-diaminobenzene and 0.1 g of dry LiCl are added under inert atmosphere to 100 ml of dry N-methylpyrrolidone (NMP) and 30 ml of dry pyridine and cooled to 5° C. 2.23 g (11 mmol) of cis-4-tert-butylcyclohexylcarbonyl chloride is added.

The reaction mixture is heated to 70° C. and stirred overnight. After 12 h the reaction mixture is added to 1500 ml of ice water. The precipitate is filtered off and dried. Customary work-up (boiling in 500 ml methanol twice) gives the desired product as a white powder.

Trans-content: 33.4% (according to $^1$H-NMR).

Melting point: 297° C.

MS(EI): 621 (M$^+$).

Decomposition temperature: 394° C.

Example C

This example demonstrates the preparation of cis-4-tert-butylcyclohexylcarbonylamino-3,5-bis[trans-4-tert-butylcyclohexylcarbonylamino]benzene.

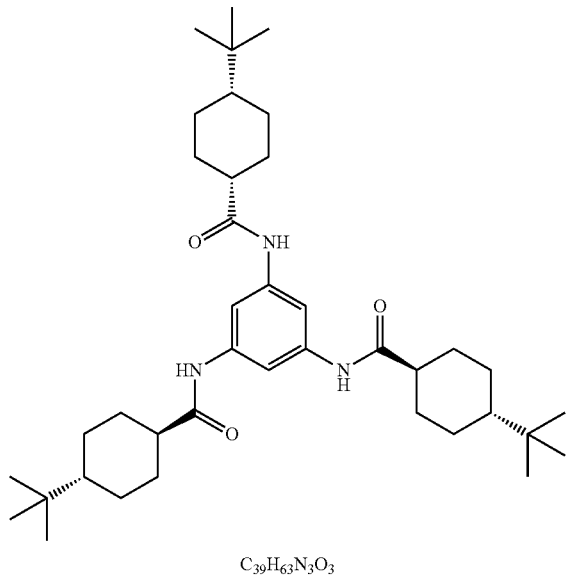 [SMILES: CC(C)(C)[C@H]1CC[C@@H](C(=O)Nc2cc(NC(=O)[C@H]3CC[C@H](C(C)(C)C)CC3)cc(NC(=O)[C@H]3CC[C@H](C(C)(C)C)CC3)c2)CC1 ; "C39H63N3O3"]

$C_{39}H_{63}N_3O_3$ a) cis-4-tert-butylcyclohexylcarbonylamino-3,5-dinitrobenzene is obtained from 5 g (27.3 mmol) of 3,5-dinitroaniline, 6.6 g (32.8 mmol) of cis-4-tert-butylcyclohexylcarbonyl chloride, 5 ml of pyridine, 200 ml of dried THF and 0.1 g of LiCl. The acylation is carried out as described in Example A.

b) 6.5 g (18.6 mmol) of the product obtained under a) is hydrogenated in 200 ml THF p.a. and 40 ml MeOH with 0.6 g Pd/C (10 wt %) at 35° C. in analogy to Example A.

The reaction mixture is transferred under inert atmosphere into a flask and filtered over 40 g of aluminum oxide (Alox N) to remove the activated carbon, the catalyst and water.

c) 3.3 g (11.4 mmol) of cis-4-tert-butylcyclohexylcarbonylamino-3,5-diaminobenzene and 0.1 g of dry LiCl are added under inert atmosphere to 200 ml of dry N-methylpyrrolidone (NMP) and 30 ml of dry pyridine and cooled to 5° C. 5.3 g (26.2 mmol) of trans-4-tert-butylcyclohexylcarbonyl chloride is added.

First the reaction mixture is heated to 100° C. and stirred for 2 h. Subsequently, the reaction mixture is cooled to 70° C. and stirred overnight. After 12 h the reaction mixture is added to 1500 ml of ice water. The precipitate is filtered off and dried. Customary work-up (recrystallization in ethanol) gives the desired product as a white powder.

Trans-content: 66.6% (according to $^1$H-NMR).

Melting point: 320° C.

MS(EI): 621 (M$^+$).

Decomposition temperature: 389° C.

Example D

This example demonstrates the preparation of 1,3,5-tris[trans-4-tert-butylcyclohexylcarbonylamino]benzene.

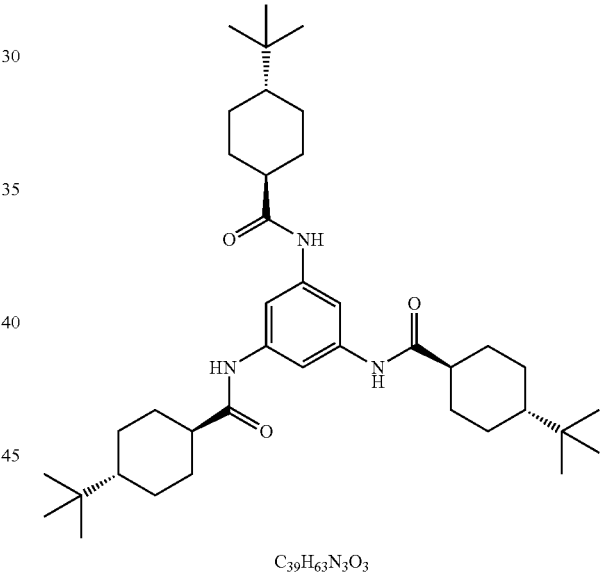

$C_{39}H_{63}N_3O_3$ 1.7 g (13.8 mmol) of 1,3,5-triaminobenzene (see Example A) and 0.1 g of dry LiCl are added under inert atmosphere to 100 ml of dry N-methylpyrrolidone (NMP) and 30 ml of dry pyridine and cooled to 5° C. 9.4 g (46 mmol) of trans-4-tert-butylcyclohexylcarbonyl chloride is added.

The reaction mixture is heated to 80° C. and stirred overnight. After 12 h the reaction mixture is added to 1500 ml of ice water. The precipitate is filtered off and dried. Customary work-up (recrystallization from acetone) gives the desired product as a white powder.

Trans-content: 100%. (according to $^1$H-NMR)

Melting point: 320° C.

MS(EI): 621 (M$^+$).

Decomposition temperature: 402° C.

Example E

This example demonstrates the preparation of 1,3,5-tris[4-tert-butylcyclohexylcarbonylamino]benzene.

Example F

This example demonstrates the preparation of 1,3,5-tris[4-tert-butylcyclohexylcarbonylamino]benzene.

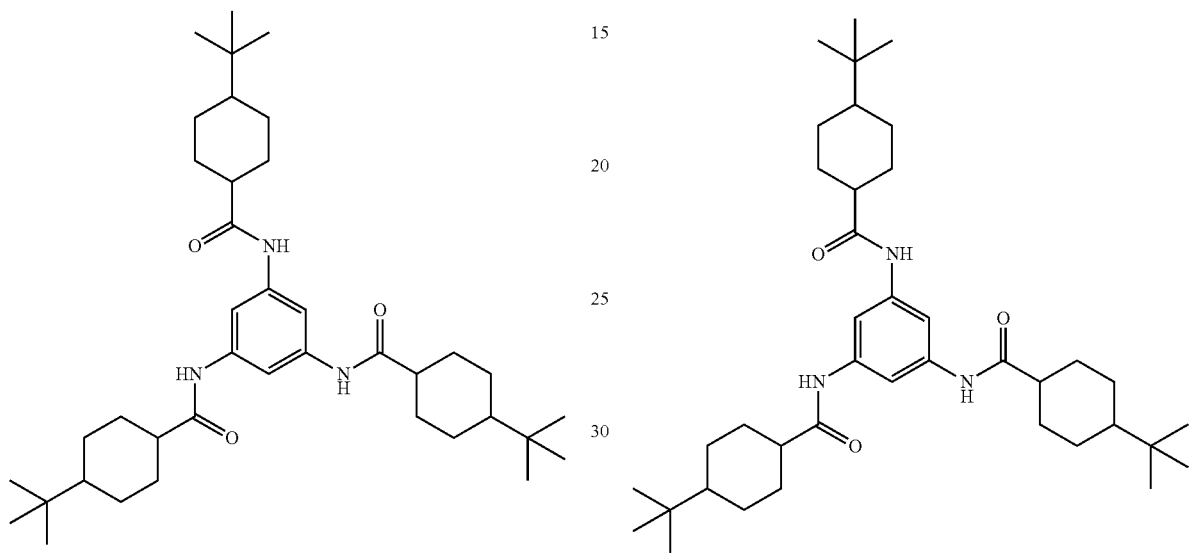

(mixture of four isomers)—$C_{39}H_{63}N_3O_3$ 1.65 g (13.4 mmol) of 1,3,5-triaminobenzene (see Example A) and 0.1 g of dry LiCl are added under inert atmosphere to 100 ml of dry N-methylpyrrolidone (NMP) and 30 ml of dry pyridine and cooled to 5° C. 8.9 g (44 mmol) of a cis/trans mixture (70%/30%) of 4-tert-butylcyclohexylcarbonyl chloride is added.

The reaction mixture is heated to 80° C. and stirred overnight. After 12 h the reaction mixture is added to 1000 ml of ice water. The precipitate is filtered off and dried. For customary work-up the product was boiled in methanol and subsequently hot filtrated. The undissolved residue was boiled in 2l methanol for 2 h, cooled to room temperature and filtered yielding the product as a white powder. The product consists of four different isomers.

Trans-content: 7.3% (according to $^1$H-NMR).
Melting point: 329° C.
MS(EI): 621 (M$^+$).
Decomposition temperature: 381° C.

(mixture of four isomers)—$C_{39}H_{63}N_3O_3$ 1.73 g (14.1 mmol) of 1,3,5-triaminobenzene (see Example A) and 0.1 g of dry LiCl are added under inert atmosphere to 100 ml of dry N-methylpyrrolidone (NMP) and 30 ml of dry pyridine and cooled to 5° C. 9.42 g (46.6 mmol) of a cis/trans mixture (50%/50%) of 4-tert-butylcyclohexylcarbonyl chloride is added.

The reaction mixture is heated to 80° C. and stirred overnight. After 12 h the reaction mixture is added to 1000 ml of ice water. The precipitate is filtered off and dried. Afterwards the product was boiled in 1000 ml methanol. For customary work-up the slightly yellow powder was sublimed (temperature gradient 290° C.-110° C.-25° C.) for 12 h yielding the product as a white powder.

The product consists of four different isomers.

Trans-content: 6.5% (according to $^1$H-NMR).
Melting point: 338° C.
MS(EI): 621 (M$^+$).
Decomposition temperature: 381° C.

Example G

This example demonstrates the preparation of 1,3,5-tris[cis-4-iso-propylcyclohexylcarbonylamino]benzene.

Example H

This example demonstrates the preparation of 1,3,5-tris[trans-4-iso-propylcyclohexylcarbonylamino]benzene.

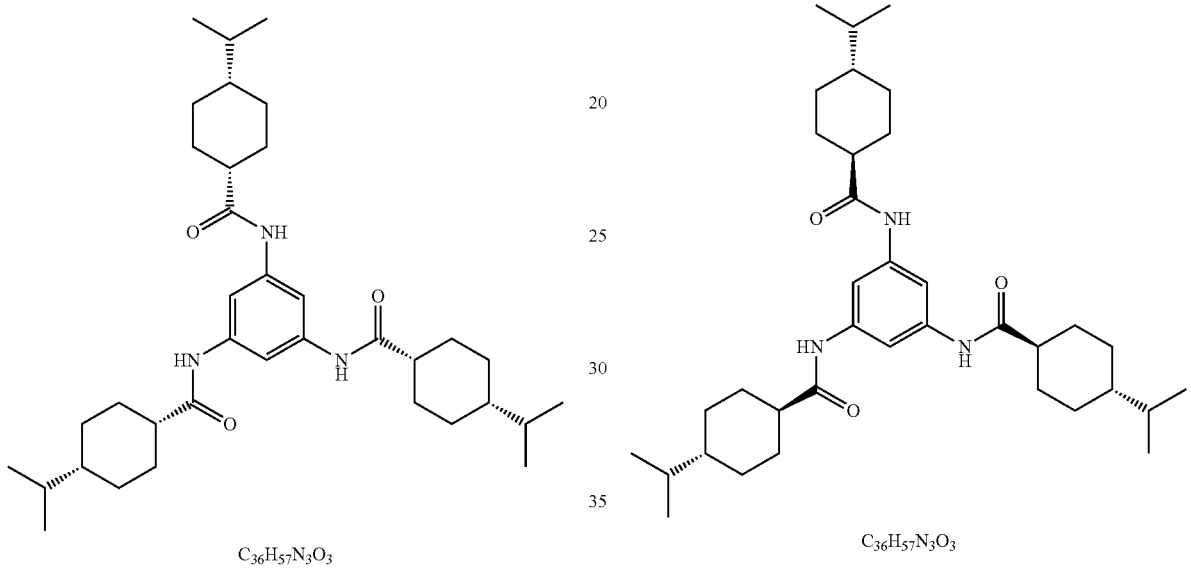

$C_{36}H_{57}N_3O_3$ $C_{36}H_{57}N_3O_3$ 1.08 g (8.7 mmol) of 1,3,5-triaminobenzene (see Example A) and 0.1 g of dry LiCl are added under inert atmosphere to 100 ml of dry tetrahydrofurane (THF) and 10 ml of dry triethylamine and cooled to 5° C. 5.47 g (29.0 mmol) of cis-4-iso-propylcyclohexylcarbonyl chloride is added.

The reaction mixture is boiled under reflux and stirred overnight.

After 12 h the solvent is evaporated and the residue is added to water and stirred for 15 min. Afterwards the residue is boiled in 500 ml methanol. The residue is filtered off and dried. Customary work-up (recrystallization from acetone) gives the desired product as a white powder.

Trans-content: 0% (according to $^1$H-NMR).

Melting point: 265° C.

MS(EI): 579 (M$^+$).

Decomposition temperature: 401° C.

1.83 g (14.8 mmol) of 1,3,5-triaminobenzene (see Example A) and 0.1 g of dry LiCl are added under inert atmosphere to 200 ml of dry tetrahydrofurane (THF) and 15 ml of dry triethylamine and cooled to 5° C. 10.24 g (54.3 mmol) of trans-4-iso-propylcyclohexylcarbonyl chloride is added.

The reaction mixture is boiled under reflux and stirred overnight.

After 12 h the solvent is evaporated and the residue is added to water and stirred for 15 min. Afterwards the residue is boiled in 500 ml hexane. The residue is filtered off and dried. Customary work-up (recrystallization from p-xylene and precipitation in methanol/water) gives the desired product as a white powder.

Trans-content: 100% (according to $^1$H-NMR).

Melting point: 274° C.

MS(EI): 579 (M$^+$).

Decomposition temperature: 396° C.

Example I

This example demonstrates the preparation of 1,3,5-tris[4-iso-propylcyclohexylcarbonylamino]benzene.

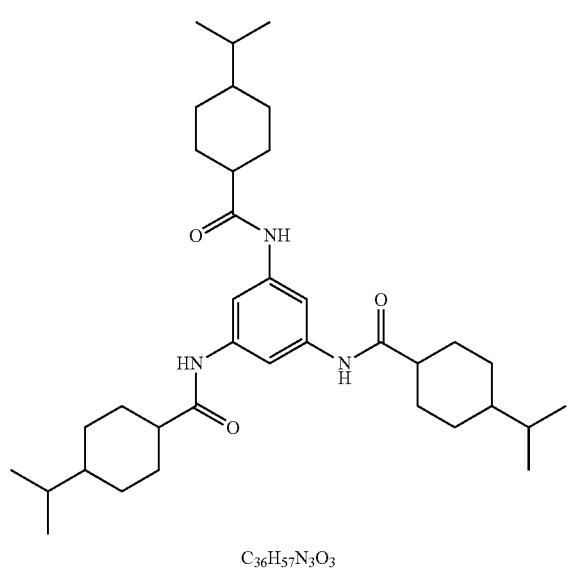 [SMILES: CC(C)C1CCC(C(=O)Nc2cc(NC(=O)C3CCC(C(C)C)CC3)cc(NC(=O)C3CCC(C(C)C)CC3)c2)CC1 ; "C36H57N3O3"]

C$_{36}$H$_{57}$N$_3$O$_3$ 1.7 g (13.8 mmol) of 1,3,5-triaminobenzene (See Example A) and 0.1 g of dry LiCl are added under inert atmosphere to 250 ml of dry tetrahydrofurane (THF) and 15 ml of dry triethylamine and cooled to 5° C. 8.6 g (45.5 mmol) of a cis/trans mixture (50%/50%) of 4-iso-propylcyclohexylcarbonyl chloride is added.

The reaction mixture is boiled under reflux and stirred overnight.

After 12 h the solvent is evaporated and the residue is added to water and stirred for 15 min. Afterwards the residue is boiled in 300 ml hexane. The residue is filtered off and dried. Afterwards the residue is added to 400 ml DMF/water (1/10), filtered off and dried, whereby the desired product is obtained as a white powder.

Trans-content: 18.4% (according to $^1$H-NMR).
Melting point: 244° C.
MS(EI): 579 (M$^+$).
Decomposition temperature: 390° C.

Example J

This example demonstrates the preparation of cis-rich 1,3,5-tris[4-iso-propylcyclohexylcarbonylamino]benzene.

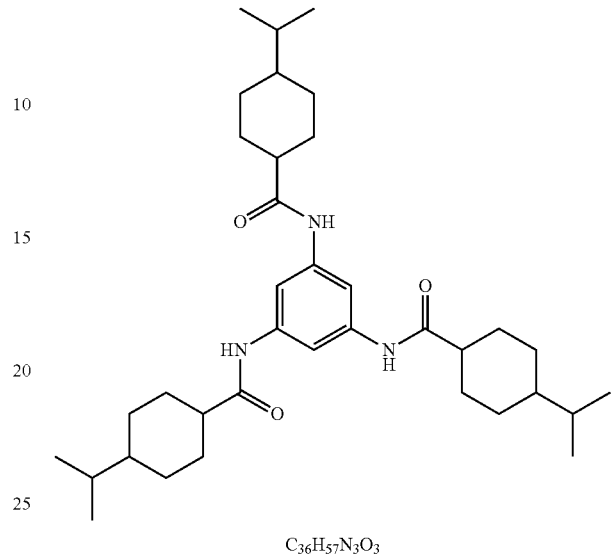

C$_{36}$H$_{57}$N$_3$O$_3$ 0.5 g of the product from Example H was stirred in 200 ml isopropanol p.a. at room temperature for 2 hours. The residue was filtered off and dried, yielding the cis-rich product as a white powder.

Trans-content: 7.7% (according to $^1$H-NMR).
Melting point: 247° C.
MS(EI): 579 (M$^+$).
Decomposition temperature: 390° C.

Example K

This example demonstrates the preparation of 1,3,5-tris[trans-4-n-propylcyclohexylcarbonylamino]benzene.

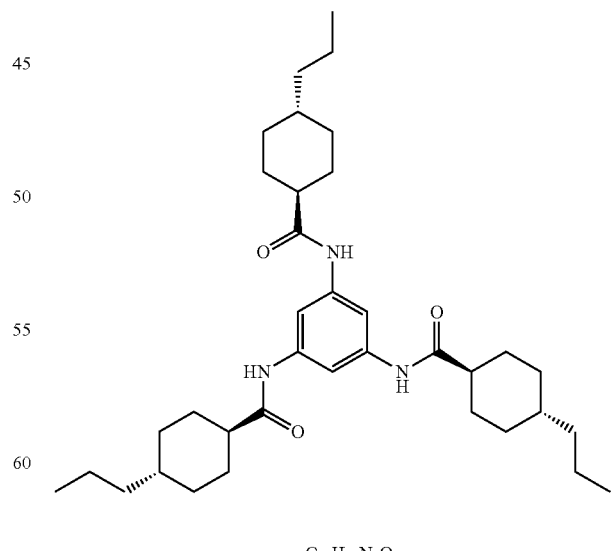

C$_{36}$H$_{57}$N$_3$O$_3$ 1.83 g (14.8 mmol) of 1,3,5-triaminobenzene (see Example A) and 0.1 g of dry LiCl are added under inert atmosphere to 200 ml of dry tetrahydrofurane (THF) and 15 ml of dry triethylamine and cooled to 5° C. 10.24 g (54.3 mmol) of trans-4-n-propylcyclohexylcarbonyl chloride is added.

The reaction mixture is boiled under reflux and stirred overnight.

After 12 h the solvent is evaporated and the residue is added to water and stirred for 15 min. Afterwards the residue is boiled in 500 ml hexane. The residue is filtered off and dried. Customary work-up (recrystallization from p-xylene and precipitation in methanol/water) gives the desired product as a white powder.

Trans-content: 100% (according to $^1$H-NMR).
Melting point: 241° C.
MS(EI): 579 (M$^+$).
Decomposition temperature: 391° C.

Example L

This example demonstrates the preparation of 1,3,5-tris[n-propylcyclohexylcarbonylamino]benzene

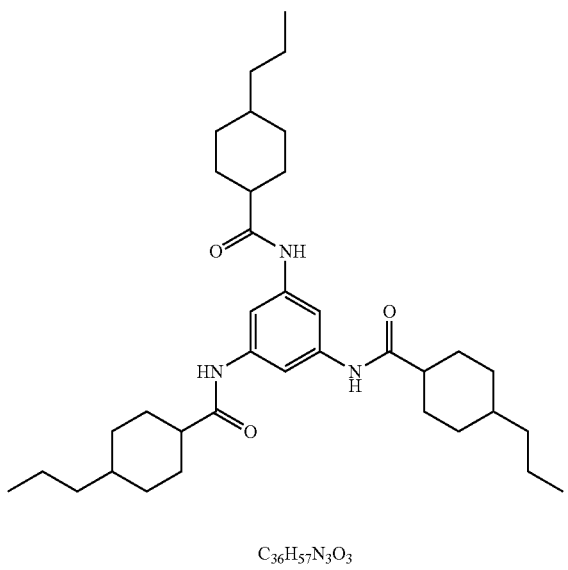 [SMILES: CCCC1CCC(C(=O)Nc2cc(NC(=O)C3CCC(CCC)CC3)cc(NC(=O)C3CCC(CCC)CC3)c2)CC1 ; "C36H57N3O3"]

$C_{36}H_{57}N_3O_3$ 1.7 g (13.8 mmol) of 1,3,5-triaminobenzene (See Example A) and 0.1 g of dry LiCl are added under inert atmosphere to 250 ml of dry tetrahydrofurane (THF) and 15 ml of dry triethylamine and cooled to 5° C. 8.6 g (45.5 mmol) of a cis/trans mixture (50%/50%) of 4-n-propylcyclohexylcarbonyl chloride is added.

The reaction mixture is boiled under reflux and stirred overnight.

After 12 hours the solvent is evaporated and the residue is added to water and stirred for 15 minutes. Afterwards the residue is boiled in 500 ml water. The residue is filtered off and dried. Customary work-up (purification via column chromatography with hexane/ethyl acetate 10:1) gives the desired product as a white powder.

Trans-content: 38.5% (according to $^1$H-NMR).
Melting point: 216° C.
MS(EI): 579 (M$^+$).
Decomposition temperature: 354° C.

Example M

This example demonstrates the preparation of tert-butylcarbonylamino-3,5-bis[cis-4-tert-butylcyclohexylcarbonylamino]benzene.

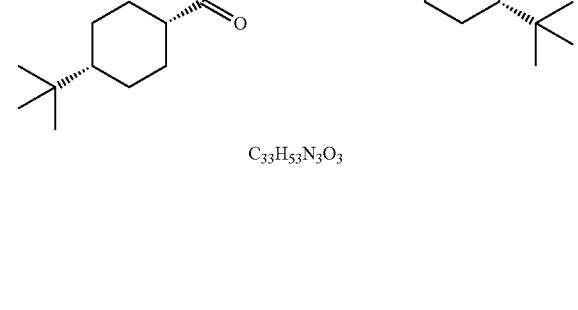

$C_{33}H_{53}N_3O_3$ a) 15.0 g (81.9 mmol) of 3,5-dinitroaniline and a tip of a spatula of dry LiCl are added under inert atmosphere to tetrahydrofurane (THF). 10 ml of dry pyridine is added and the solution is cooled to 5° C. Afterwards, 10.86 g (90.1 mmol) of pivaloyl chloride is added.

The reaction mixture is heated to 80° C. and stirred overnight. After 12 h the reaction mixture is added to ice water. The precipitate is filtered off and dried.

b) 20.19 g (75.0 mmol) of the product obtained under a) is hydrogenated in 300 ml THF p.a. and 50 ml MeOH with 2.0 g Pd/C (10 wt %) at 35° C. in analogy to Example A. The reaction mixture is transferred under inert atmosphere into a flask and filtered over 40 g of aluminum oxide (Alox N) to remove the activated carbon, the catalyst and water.

c) 9.17 g (44.2 mmol) of tert-butylcarbonylamino-3,5-diaminobenzene and 0.1 g of dry LiCl are added under inert atmosphere to 200 ml of dry NMP, 13 ml of dry pyridine and 9.60 g (88.4 mmol) trimethylchlorsilane and cooled to 5° C. 19.74 g (97.3 mmol) of cis-4-tert-butylcyclohexylcarbonyl chloride is added. The reaction mixture is heated to 70° C. and stirred overnight. After 12 h the reaction mixture is added to 2000 ml of ice water. The precipitate is filtered off and dried. Customary work-up (boiling in methanol) gives the desired product as a white powder.

Trans-content: <3% (according to $^1$H-NMR).
Melting point: 288° C.
MS(EI): 539 (M+).
Decomposition temperature: 382° C.

Example N

This example demonstrates the preparation of cis-4-tert-butylcyclohexylcarbonylamino-3,5-bis[4-tert-butylcarbonylamino]benzene.

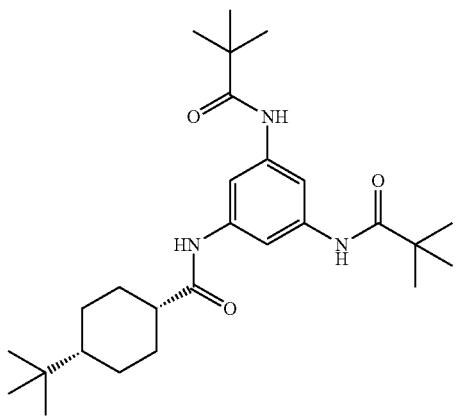

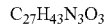

a) 12.4 g (67.5 mmol) of 3,5-dinitroaniline and a tip of a spatula of dry LiCl are added under inert atmosphere to tetrahydrofurane (THF). 10 ml of dry pyridine is added and the solution is cooled to 5° C. Afterwards, 15.0 g (74.2 mmol) of cis-4-tert-butylcyclohexylcarbonyl chloride is added. The reaction mixture is heated to 80° C. and stirred overnight. After 12 h the reaction mixture is added to ice water. The precipitate is filtered off and dried.

b) 22.0 g (63.0 mmol) of the product obtained under a) is hydrogenated in 500 ml THF p.a. and 50 ml MeOH with 2.2 g Pd/C (10 wt %) at 35° C. in analogy to Example A. The reaction mixture is transferred under inert atmosphere into a flask and filtered over 40 g of aluminum oxide (Alox N) to remove the activated carbon, the catalyst and water.

c) 7.88 g (26.4 mmol) of cis-4-tert-butylcyclohexylcarbonylamino-3,5-diaminobenzene and 0.1 g of dry LiCl are added under inert atmosphere to 100 ml of dry NMP and 5 ml of dry pyridine and cooled to 5° C. 7.00 g (58.0 mmol) of pivaloyl chloride is added. The reaction mixture is heated to 70° C. and stirred overnight. After 12 h the reaction mixture is added to 2000 ml of ice water. The precipitate is filtered off and dried. Customary work-up (boiling in methanol) gives the desired product as a white powder.

Trans-content: <3% (according to $^1$H-NMR).
Melting point: 312° C.
MS(EI): 457 (M+).
Decomposition temperature: 357° C.

Example O

This example demonstrates the nucleation of polypropylene by compounds according to the present invention:

The polymer powder (propylene random copolymer (racoRD208CF—*Borealis*)) with a melt flow index of 8 g/min (measured at 230° C. and 2.16 kg), is intensely mixed with adequate amounts of the respective trisamide compound, so that polymer-additive-mixtures, which contain 0.01-1 wt. % additive, were obtained. Series of mixtures of different concentrations were produced by dilution of initial batches, typically containing 0.01 wt. % to 1 wt. % additive, by addition of defined quantities of neat polymer and the additive containing initial batch.

Compounding of the formulations is performed at 230° C. (melt temperature) on a co-rotating laboratory twin-screw extruder, such as the Xplore Micro Compounder 15 ml from DSM®, for a period of about 5 min. Samples of the extruded strands are used to determine the polymer crystallization temperature by differential scanning calorimetry (DSC). Differential Scanning Calorimetry (DSC):

A Perkin-Elmer DSC Instrument® (Diamond DSC), operated in a dry nitrogen atmosphere, is used for the analysis of the crystallization behavior of the various mixtures and control samples, according to standard procedures. About 5 to 10 mg of the sample is sealed into an aluminum cup, heated from 50° C. to 250° C. at a rate of 10° C./min, held at 250° C. for 5 min, and then subsequently cooled at a rate of 10° C./min to 50° C. The data represented as polymer crystallization temperatures, $T_c$, are the peak temperatures of the exotherms in the thermograms that are recorded upon cooling.

TABLE 1

Trisamide compound concentration and crystallization temperatures for exemplary polymer compositions.

| Sample | Trisamide Compound | Trisamide Compound Concentration (wt. %) | Crystallization Temperature (° C.) |
|---|---|---|---|
| Control | — | — | 95.6 |
| 1 | Ex. A | 0.05 | 114.2 |
| 2 | Ex. G | 0.2 | 115.2 |
| 3 | Ex. B | 0.2 | 102.3 |
| 4 | Ex. C | 0.02 | 98.4 |
| 5 | Ex. D | 0.2 | 106.4 |
| 6 | Ex. E | 0.06 | 114.0 |
| 7 | Ex. F | 0.06 | 113.0 |
| 8 | Ex. H | 0.2 | 105.1 |
| 9 | Ex. I | 0.2 | 100.3 |
| 10 | Ex. J | 0.2 | 111.9 |
| 11 | Ex. K | 0.2 | 101.2 |
| 12 | Ex. L | 0.2 | 100.4 |
| 13 | Ex. M | 0.2 | 106.7 |
| 14 | Ex. N | 0.2 | 101.8 |

As can be seen from the data in Table 1, the polymer compositions containing a trisamide compound according to the invention (i.e., Samples 1-14) exhibited higher crystallization temperatures than the unnucleated polymer (i.e., Control). Indeed, some of the trisamide compounds of the invention imparted an appreciable increase in the polymer crystallization temperature at concentrations as low as (0.02 wt. %) (see, e.g., Sample 4). Furthermore, some of the trisamide compounds of the invention increased the polymer crystallization temperature by seven degrees Centigrade or more (see, e.g., Samples 1, 2, 6, and 7). These data demonstrate that the trisamide compounds of the invention are effective nucleating agents for polymers.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as openended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A composition comprising:
(a) trisamide compounds of general formula (III)

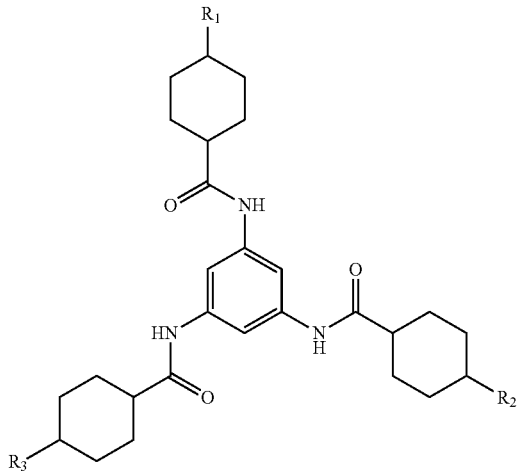

(III)

wherein $R_1$, $R_2$, and $R_3$ are univalent groups other than hydrogen, and (b) a polymer, wherein (i) the composition comprises a trisamide compound of general formula (III) wherein $R_1$, $R_2$, and $R_3$ are each in the cis position relative to the bond to the carbonyl carbon attached to the cyclohexanediyl ring; and (ii) 33.4% or less of the $R_1$, $R_2$, and $R_3$ groups of the trisamide compounds of general formula (III) present in the composition are in the trans position relative to the bond to the carbonyl carbon attached to the cyclohexanediyl ring.

2. The composition of claim 1, wherein the polymer is a thermoplastic polymer.

3. The composition of claim 2, wherein the polymer is a polyolefin polymer.

4. The composition of claim 3, wherein the polymer is a polypropylene polymer.

5. The composition of claim 1, wherein the trisamide compounds are present in the composition in an amount of at least 0.05 wt. % relative to the total weight of the composition.

6. The composition of claim 1, wherein $R_1$, $R_2$, and $R_3$ are independently selected from the group consisting of: $C_1$-$C_{20}$ alkyl groups unsubstituted or substituted by one or more hydroxy; $C_2$-$C_{20}$ alkenyl groups unsubstituted or substituted by one or more hydroxy; $C_2$-$C_{20}$ alkyl groups interrupted by oxygen or sulfur; $C_1$-$C_{20}$ alkyl groups substituted by one or more halogens; halogens; trimethylsilyl; and cyano.

7. The composition of claim 6, wherein $R_1$, $R_2$, and $R_3$ are independently selected from the group consisting of $C_1$-$C_6$ alkyl groups; branched $C_3$-$C_{20}$ alkyl groups unsubstituted or substituted by one or more hydroxy; $C_1$-$C_{12}$ alkyl groups substituted by one or more halogens; halogens; trimethylsilyl; and cyano.

8. The composition of claim 7, wherein $R_1$, $R_2$, and $R_3$ are independently selected from the group consisting of $C_1$-$C_3$ alkyl groups; branched $C_3$-$C_{12}$ alkyl groups; fluorine; chlorine; and trimethylsilyl.

9. The composition of claim 8, wherein $R_1$, $R_2$, and $R_3$ are independently selected from the group consisting of branched $C_3$-$C_5$ alkyl groups.

10. The composition of claim 9, wherein the composition comprises 1,3,5-tris[cis-4-tert-butylcyclohexylcarbonylamino]benzene.

11. The composition of claim 1, wherein the composition does not contain trisamide compounds of general formula (III) in which one or more of $R_1$, $R_2$, or $R_3$ is in the trans position relative to the bond to the carbonyl carbon attached to the cyclohexanediyl ring.

* * * * *